United States Patent [19]
Mahurkar

[11] Patent Number: 5,197,951
[45] Date of Patent: Mar. 30, 1993

[54] SIMPLE DOUBLE LUMEN CATHETER

[76] Inventor: Sakharam D. Mahurkar, 6171 N. Sheridan Rd. - #1112, Chicago, Ill. 60660

[21] Appl. No.: 834,202

[22] Filed: Feb. 27, 1986

Related U.S. Application Data

[63] Continuation of Ser. No. 561,480, Dec. 14, 1983, abandoned.

[51] Int. Cl.$^5$ ............................................ A61M 11/00
[52] U.S. Cl. ........................................ 604/93; 604/43; 604/283; 606/94
[58] Field of Search .............................. 604/93, 43–45, 604/280–282; 606/191, 192

[56] References Cited

U.S. PATENT DOCUMENTS

| D. 250,349 | 11/1978 | McFarlane | D24/54 |
|---|---|---|---|
| D. 254,444 | 3/1980 | Levine | D24/54 |
| 256,590 | 4/1882 | Pfarre | |
| D. 256,617 | 8/1980 | Clemens | D24/54 |
| D. 272,651 | 2/1984 | Mahurkar | |

(List continued on next page.)

FOREIGN PATENT DOCUMENTS

| 834211 | 2/1976 | Belgium | 128/221 |
|---|---|---|---|
| 1092927 | 1/1981 | Canada | 604/43 |
| 50089 | 8/1982 | Canada | |
| 1150122 | 7/1983 | Canada | 128/81 |
| 1167727 | 5/1984 | Canada | 128/80 |
| 36642 | 9/1981 | European Pat. Off. | 604/43 |
| 0079719 | 11/1982 | European Pat. Off. | |
| 935625 | 11/1955 | Fed. Rep. of Germany | |
| 2259865 | 6/1974 | Fed. Rep. of Germany | 128/221 |
| MR19346 | 6/1982 | Fed. Rep. of Germany | |
| 592193 | 4/1925 | France | 128/214.2 |
| 1285953 | 7/1962 | France | |
| 1508959 | 1/1968 | France | |
| 2285148 | 4/1976 | France | |
| 2297640 | 8/1976 | France | |
| 821344 | 4/1982 | France | |
| 55-88771 | 7/1980 | Japan | 128/348 |
| 688450 | 3/1952 | United Kingdom | |
| 1419702 | 12/1975 | United Kingdom | 128/221 |
| 1006219 | 3/1983 | United Kingdom | |
| 1017315 | 5/1983 | U.S.S.R. | |

OTHER PUBLICATIONS

McIntosh et al., "Double Lumen Catheter," *J.A.M.A.*, Feb. 21, 1959, pp. 137/835–138/836.

*Dorland's Illustrated Medical Dictionary*, 25th Ed., W. B. Saunders Co., Philadelphia, 1974, p. 274.
Brenner & Rector, *The Kindney*, vol. III, W. B. Saunders Co., Philadelphia, 1976, p. 164.
*ASAIO Abstracts*, vol. 5, 22nd Annual Meeting, San Franciso, Calif., Apr. 1-3, 1976, p. 52.
Tohuko, J., "Single Two–Lumen Cannula Dialysis", Aug. 1974.
Tsuchida et al., "Single Two–Lumen Cannula Dialysis", Toboku Journal Exp. Med., 1974, pp. 114, 159–101.
Tsuchida et al. "Design of a Two–Lumen–Piercing Needle That Is Capable of Carrying Out Dialysis By Single Puncture", Journal of The Urological Society of Japan, vol. 65 (12), 1974, pp. 805–807.
Kaplan et al., "A Co-Axial Dual Flow Catheter/Cannula For Single Puncture Dialysis", Dialysis & Transplantation, Dec./Jan. 1977, pp. 38–40, 42, 84.
"Terumo Coaxial Dual Flow Catheter", Terumo America, Inc., Apr., 1979 (two pages).
"Portner-Koolpe Biliary Biopsy Set", Cook Inc. (1 page).

Primary Examiner—C. Fred Rosenbaum
Assistant Examiner—Chalin Smith
Attorney, Agent, or Firm—Arnold, White & Durkee

[57] ABSTRACT

A double lumen catheter comprising an elongated cylindrical tube enclosing first and second lumens separated by an internal divider, the proximal end of the elongated tube connecting to two separate connecting tubes communicating with the respective first and second lumens for the injection and removal of blood, the first lumen extending from the proximal end of the elongated tube to a first opening formed in the side wall of the tube and at the distal end of the elongated tube, and the second lumen extending from the proximal end of the elongated tube to a second opening spaced a sufficient distance away from the first opening, in the longitudinal direction, to prevent mixing of the returned blood with the blood taken in, the distal end portion of the tube beyond the distal end of the second lumen continuing the cylindrical configuration of the tube to the distal end of the first lumen so as to form a blunt circular end on the tube to prevent the end of the catheter from traumatizing or becoming caught in the walls of a blood vessel into which the catheter is inserted.

13 Claims, 1 Drawing Sheet

U.S. PATENT DOCUMENTS

| | | |
|---|---|---|
| 701,075 | 5/1902 | McCully . |
| 998,339 | 7/1911 | Hollins .................. 27/24 A |
| 1,045,326 | 11/1912 | Ruflin . |
| 1,093,538 | 4/1914 | Clough . |
| 1,290,647 | 1/1919 | Nyvall .................. 128/214 RX |
| 1,922,084 | 8/1933 | Gerow .................. 128/349 |
| 2,175,726 | 10/1939 | Gebauer .................. 128/349 B |
| 2,230,218 | 2/1941 | Asche .................. 128/276 |
| 2,409,343 | 10/1946 | Curtis .................. 128/214 |
| 2,473,742 | 6/1949 | Auzin .................. 128/349 |
| 2,474,665 | 6/1949 | Guarino .................. 128/DIG. 3 |
| 2,564,977 | 8/1951 | Hsu Hu .................. 128/221 X |
| 2,590,895 | 4/1952 | Scarpellino .................. 128/221 |
| 2,625,932 | 1/1953 | Salisbury .................. 128/214.2 |
| 2,716,983 | 9/1955 | Windischman et al. .................. 128/221 |
| 2,819,718 | 1/1958 | Goldman .................. 128/350 |
| 2,930,378 | 3/1960 | Buyers .................. 128/354 |
| 3,042,045 | 7/1962 | Sheridan .................. 128/349 |
| 3,175,554 | 3/1965 | Stewart .................. 128/2 |
| 3,314,430 | 4/1967 | Alley et al. .................. 128/350 |
| 3,324,853 | 6/1967 | Czorny et al. .................. 128/214.4 |
| 3,331,371 | 7/1967 | Rocchi et al. .................. 128/349 |
| 3,359,974 | 12/1967 | Khalil .................. 128/2.05 |
| 3,394,705 | 7/1968 | Abramson .................. 128/349 |
| 3,435,826 | 1/1969 | Fogarty .................. 128/348 |
| 3,437,088 | 4/1969 | Bielinski .................. 128/2 |
| 3,448,739 | 6/1969 | Stark et al. .................. 128/2.05 |
| 3,452,756 | 7/1969 | Harautuneian .................. 128/349 |
| 3,463,152 | 8/1969 | Sorenson .................. 128/214.4 |
| 3,467,101 | 9/1969 | Fogarty et al. .................. 128/348 |
| 3,543,758 | 12/1970 | McWhorter .................. 128/349 |
| 3,543,759 | 12/1970 | McWhorter .................. 128/349 |
| 3,550,591 | 12/1970 | MacGregor .................. 128/214.4 |
| 3,566,874 | 3/1971 | Sheperd et al. .................. 128/349 |
| 3,593,713 | 7/1971 | Bogoff et al. .................. 128/246 |
| 3,599,620 | 8/1971 | Balin .................. 128/349 B |
| 3,634,924 | 1/1972 | Blake et al. .................. 29/447 |
| 3,683,908 | 8/1972 | Michael et al. .................. 128/145.7 |
| 3,726,281 | 4/1973 | Norton et al. .................. 128/349 R |
| 3,746,003 | 7/1973 | Blake et al. .................. 128/349 B |
| 3,756,234 | 9/1973 | Kopp .................. 128/214 R |
| 3,771,527 | 11/1973 | Ruisi .................. 604/43 |
| 3,774,605 | 11/1973 | Jewett .................. 128/214.4 |
| 3,799,172 | 3/1974 | Szpur .................. 128/349 R |
| 3,804,097 | 4/1974 | Rudie .................. 128/350 R |
| 3,823,720 | 7/1974 | Tribble .................. 128/350 R |
| 3,828,767 | 8/1974 | Spiroff .................. 128/2.05 |
| 3,830,234 | 8/1974 | Kopp .................. 128/214 R |
| 3,875,938 | 4/1975 | Mellor .................. 128/214.4 |
| 3,885,567 | 5/1975 | Ross .................. 128/278 |
| 3,896,815 | 7/1975 | Fettel et al. .................. 128/348 |
| 3,978,863 | 9/1976 | Fettel et al. .................. 128/348 |
| 4,004,588 | 1/1977 | Alexander .................. 128/241 |
| 4,016,879 | 4/1977 | Mellor .................. 128/214.4 |
| 4,027,668 | 6/1977 | Dunn .................. 128/214 R |
| 4,037,599 | 7/1977 | Raulerson .................. 128/214.4 |
| 4,057,065 | 11/1977 | Thow .................. 128/348 |
| 4,072,146 | 2/1978 | Howes .................. 128/2.05 D |
| 4,096,860 | 6/1978 | McLaughlin .................. 128/214.4 |
| 4,098,275 | 7/1978 | Consalvo .................. 128/221 X |
| 4,099,528 | 7/1978 | Sorenson et al. .................. 128/214.4 |
| 4,100,246 | 7/1978 | Frisch .................. 264/230 |
| 4,116,068 | 9/1978 | Megahed .................. 73/425.4 P |
| 4,134,402 | 1/1979 | Mahurkar .................. 604/44 |
| 4,144,884 | 3/1979 | Tersteegen et al. .................. 128/214.4 |
| 4,168,703 | 9/1979 | Kenigsberg .................. 128/748 |
| 4,180,068 | 12/1979 | Jacobsen et al. .................. 128/214 R |
| 4,202,332 | 5/1980 | Tersteegen et al. .................. 128/221 X |
| 4,203,436 | 5/1980 | Grimsrud .................. 128/214 R |
| 4,217,895 | 8/1980 | Sagae et al. .................. 128/214.4 |
| 4,270,535 | 7/1981 | Bogue et al. .................. 128/214.4 |
| 4,314,555 | 2/1982 | Sagae .................. 128/214.4 |
| 4,336,036 | 6/1982 | Leeke et al. .................. 128/214 RX |
| 4,385,631 | 5/1983 | Uthmann .................. 604/284 |
| 4,403,983 | 9/1983 | Edelman et al. .................. 604/43 |
| 4,403,985 | 9/1983 | Boretos .................. 604/53 |
| 4,406,656 | 9/1983 | Hattler et al. .................. 604/280 |
| 4,419,095 | 12/1983 | Nerbergall et al. .................. 604/96 |
| 4,451,252 | 5/1984 | Martin .................. 604/43 |
| 4,484,585 | 11/1984 | Baier .................. 128/748 |
| 4,493,696 | 5/1985 | Uldall .................. 604/43 |
| 4,543,087 | 9/1985 | Sommercorn et al. .................. 604/43 |
| 4,568,329 | 2/1986 | Mahurkar .................. 604/43 |
| 4,583,968 | 4/1986 | Mahurkar .................. 604/43 |
| 4,623,327 | 11/1986 | Mahurkar .................. 604/4 |
| 4,682,978 | 7/1987 | Martin .................. 604/43 |

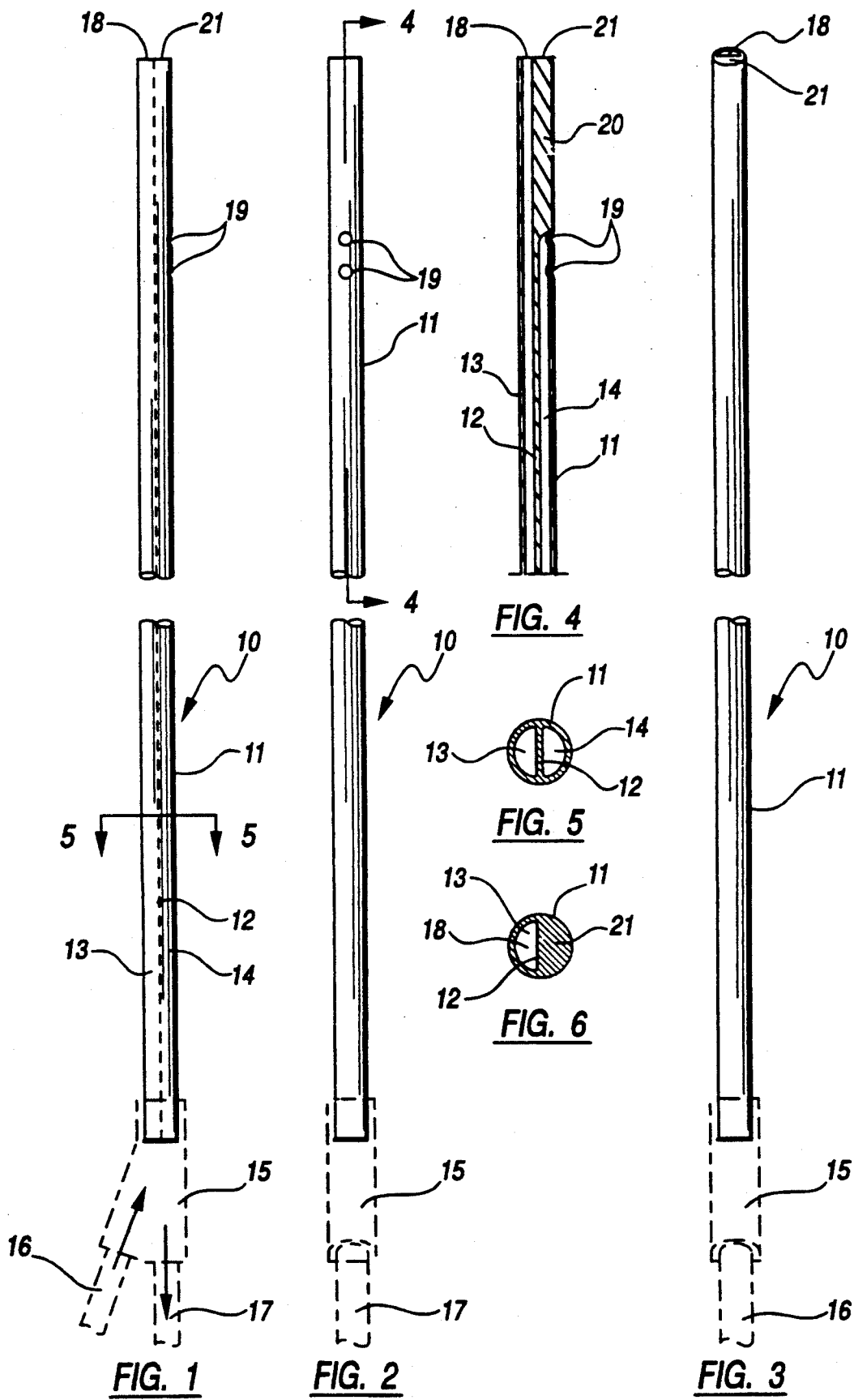

SIMPLE DOUBLE LUMEN CATHETER

RELATED APPLICATIONS

The present application is a continuating application of my copending U.S. patent application Ser. No. 561,480 filed Dec. 14, 1983.

BACKGROUND OF THE INVENTION

1. Field of Invention

The present invention relates to surgical instruments for withdrawing fluids from or introducing fluids into a cavity of the body.

2. Description of the Related Art (Information Disclosure Statement Incorporated Into The Specification per 37 C.F.R. §1.97(a))

As is well known, a catheter is a tubular, flexible, surgical instrument for withdrawing fluids from (or introducing fluids into) a cavity of the body. A double-current catheter is a catheter having two channels; one for injection and one for removal of fluid. *Dorlan's Illustrated Medical Dictionary, Twenty Fifth-Edition* (W. B. Saunders, Philadelphia 1974), p. 274. As is well known, a double-current catheter is used for removing blood from a fistula or vein for processing in a dialysis machine and returning the processed blood back to the fistula or vein. A double-current catheter suitable for this purpose is disclosed in Mahurkar, U.S. Pat. No. 4,134,402 issued Jan. 16, 1979. Mahurkar U.S. Pat. No. 4,134,402 discloses a double lumen continuous flow hemodialysis needle and cannula having contiguous lumens of different lengths formed by dividing a unitary straight tube, the shorter lumen acting as a blood intake lumen and the longer acting as a blood return lumen. A sharp penetrating bevel is provided on the distal tip for percutaneous entry into a fistula. Semi-circular lumens provide a minimal resistance to blood flow resulting in a smaller but highly efficient catheter in comparison to a coaxial double-current catheter. Hemodialysis requires, for example, a blood flow rate of about 200 ml/min or more and flow resistance less than about 100 mm of mercury.

There are numerous other United States Patents disclosing double-current catheters for hemodialysis and evidencing a long-felt need for a small, functionally efficient catheter having a minimum of insertion trauma and potential for clotting. McLaughlin, U.S. Pat. No. 4,096,860 issued Jun. 27, 1978 discloses a coaxial hemodialysis catheter said to allow a step enlargement of the opening of a blood vessel to avoid tearing and rupture of the side walls. A simultaneous flow device incorporates a hub with an extension conduit and a valve therein for receipt of a needle therethrough. The extension conduit is of sufficient size to allow the passage of the needle therethrough adjacent the interior side walls thereof with an attendant extension thereof from its opening. The needle with the extension conduit is adapted for combined insertion within a blood vessel, after which it can be withdrawn while the valve prevents the backflow of blood through the axial passage of the hub. A coaxial flow device can then be inserted within the hub conduit.

Sorensen et al., U.S. Pat. No. 4,099,528 issued Jul. 11, 1978 discloses a coaxial double lumen cannula mounted upon a hub and having a central stylet needle for penetrating a patient's vein and which is retractable after penetration.

Grimsrud, U.S. Pat. No. 4,203,436 issued May 20, 1980 discloses a hollow hypodermic needle with a divider for providing a first channel for removal of blood for treatment from a punctured blood vessel and a second channel for returning the treated blood to the blood vessel.

Uthmann, U.S. Pat. No. 4,385,631 issued May 31, 1983 discloses a hemodialysis catheter for puncturing blood vessels which includes a section insertable through a puncture opening into a blood vessel and a hose line following thereafter. This catheter has two circular lumens arranged side by side. One of the circular lumens has a sloping bevel while the other circular lumen passes slidably through a sheath integral with the first lumen. This device requires a large puncture opening and produces an inefficient relationship of flow rate to puncture area.

Jacobson et al., U.S. Pat. No. 4,180,068 issued Dec. 25, 1979 discloses a double-current hemodialysis catheter comprising a primary tube and an internal divider which also functions as a trocar and valve. The primary tube has a side opening for receiving blood and a central opening at the distal end of the primary tube. The internal divider includes a cutting end which protrudes from the distal opening when the divider is longitudinally moved to an insert position. In the insert position, blood flow is blocked.

Mahurkar, Design U.S. Pat. No. 272,651 issued Feb. 14, 1984 discloses a double lumen catheter having an outlet lumen which has an opening at the tip of the catheter and a shorter inlet lumen which terminates in a bevel substantially displaced from the tip.

Uldall U.S. Pat. No. 4,493,696 issued Jan. 15, 1985 describes a coaxial double lumen catheter in which the outer lumen is constricted at its distal end, and the tip of the inner lumen rests against the beginning of this constriction. Blood is withdrawn for processing through the outer lumen via multiple openings in the outer wall; the processed blood is returned through the inner lumen.

SUMMARY OF THE INVENTION

The primary object of the invention is to provide a simple and efficient double lumen catheter of small size which will not traumatize or become caught in the walls of a blood vessel into which the catheter is inserted, and yet is relatively easy to insert into the blood vessel.

A further object of this invention is to provide a double lumen catheter which is easy and inexpensive to manufacture.

Other objects and advantages of the invention will become apparent from the following detailed description and the accompanying drawings.

BRIEF DESCRIPTION OF DRAWINGS

In the drawings:

FIG. 1 is a front and rear elevational view of a double lumen catheter embodying my invention;

FIG. 2 is a right side elevational view of the catheter illustrated in FIG. 1;

FIG. 3 is a left side elevational view of catheter illustrated in FIG. 1;

FIG. 4 is a section taken generally along line 4—4 thereof in FIG. 2;

FIG. 5 is a section taken generally along line 5—5 in FIG. 1; and

FIG. 6 is a top view of the catheter illustrated in FIG. 1.

While the invention will be described in connection with a certain preferred embodiment, it will be understood that it is not intended to limit the invention to that particular embodiment. On the contrary, it is intended to cover all alternatives, modifications, and equivalents as may be included within the spirit and scope of the invention as defined by the appended claims.

DETAILED DESCRIPTION OF PREFERRED EMBODIMENTS

Turning now to the drawings, FIGS. 1, 2, 3 and 6 show various external views of a simple double lumen catheter, generally designated 10, in accordance with the present invention. As is conventional for a catheter, the double lumen catheter 10 has an elongated unitary hollow tube 11 which is inserted into a body cavity such as a vein. The major portion of the tube 11 is circular in cross section, as shown in FIG. 5, and has an internal planar axial divider or septum 12 defining a return lumen 13 and an inlet lumen 14 within the interior of the hollow tube 11. This divider 12 is preferably of unitary or one-piece construction with the tube 11, bisecting the tube into the two lumens 13 and 14. The transverse cross-sections of the lumens 13 and 14 are semicircular or "D" shaped (see FIG. 5) which minimizes resistance to fluid flow.

As is conventional for this type of dual lumen construction, the divider 12 extends axially along the interior of the tube 11 from a branching connector 15. The branching connector 15 connects the proximal ends of the return lumen 13 and the inlet lumen 14 to respective fluid return and inlet lines 16 and 17 which are, for example, respective venous and arterial lines of a dialysis or plasmapheresis circuit. The preferred direction of fluid circulation is indicated by dashed arrows in FIG. 1.

The hollow tube 11 includes openings or apertures at the distal end portions of the lumens 13 and 14 to permit the flow of the fluid between a body cavity (not shown) and the lumens. The return lumen 13 extends along the entire length of the tube 11 to an aperture or opening 18 at the distal end of the tube 11 as is more clearly shown in FIG. 4. The inlet lumen 14 is shorter than the return lumen 13 and terminates at a pair of apertures or openings 19 in the side wall of the tube 11. The openings are substantially displaced, in the longitudinal direction from the return aperture 18 to prevent mixing of the returned blood with the blood taken in.

In accordance with the invention, the tube 11 terminates with a blunt distal end 21 which is normal to the axis of the catheter 10. It does not have the conical tip or taper that is characteristic of other catheters. The absence of the conical tip avoids trauma and migration of the catheter into the tributaries of the veins, e.g., the blunt end prevents the end of the catheter from traumatizing or becoming caught in the walls of a blood vessel into which the catheter is inserted.

To continue the cylindrical configuration of the tube 11 all the way to the blunt distal end 21, the half of the tube which forms the intake lumen 14 forms a solid portion 20 which extends from the distal end of the lumen 14 to the blunt distal end 21 of the tube. This provides the blunt distal end 21 of the tube with a circular configuration, as can be seen in FIGS. 3 and 6, with the semi-circular cavity of the return lumen 13 opening through one half of the circle. To facilitate the flow of blood into the intake lumen 14, the solid distal end portion of the tube 11 forms a curved surface rising at its proximal end from the planar divider 12 and terminating at its distal end on the edge of the distal opening 19 in the side wall of the tube.

The dual lumen tube 11 can be formed by molding a polymeric material. Alternatively, the dual-lumen tube can be extruded with the two semi-circular lumens extending through the full length of the tube, and then the distal end of one of the lumens filled with a polymeric material to form the shorter intake lumen 14. The openings 19 can be cut in the side wall of the tube to provide the requisite access to the intake lumen.

For use in hemodialysis, the double lumen catheter 10 is introduced in the direction of blood flow in a large vein by surgically exposing the vein or, over a Seldinger's guide wire through a sheath as is conventional. The inlet opening 19 on the blood inlet lumen 14 draws the blood for processing and the processed blood is returned through the return lumen 13 and out through the hole to return the blood upstream into circulation.

What is claimed is:

1. A double lumen catheter comprising an elongated cylindrical tube of substantially uniform diameter having unitary outer walls and enclosing first and second lumens separated by a planar axial internal divider, the proximal end of said elongated tube connecting to two separate connecting tubes communicating with the respective first and second lumens, the first lumen extending from the proximal end of said elongated tube to a first opening at the distal end of said elongated tube, and the second lumen extending from the proximal end of said elongated tube to a second opening formed in the side wall of said tube and spaced in the longitudinal direction away from said first opening, the distal end portion of said tube beyond the distal end of said second lumen being formed so that no voids are present in the flow path and continuing the uniform diameter cylindrical configuration of said tube to the distal end of said first lumen so as to form a blunt circular end on the tube, and said blunt circular end being completely closed except for said first opening, to prevent the end of the catheter from traumatizing or becoming caught in the walls of a vessel into which the catheter is inserted.

2. The double lumen catheter as claimed in claim 1, wherein the distal end of said second lumen is defined by a curved surface rising at its proximal end from the planar divider and terminating at its distal end on the edge of said second opening in the side wall of said tube.

3. The double lumen catheter as claimed in claim 1, wherein the lumens are "D" shaped in cross-section.

4. The double lumen catheter as claimed in claim 1, wherein said divider in said cylindrical portion is planar, and said lumens are "D" shaped in cross-section along the entire length of said tube.

5. The double lumen catheter as claimed in claim 1, which includes multiple second openings formed in the side wall of said tube at the distal end of said second lumen.

6. The double lumen catheter as claimed in claim 1, wherein said elongated cylindrical tube is a unitary tube of one-piece construction with an internal divider.

7. The double lumen catheter as claimed in claim 1, wherein said first and second lumens are semicircular in transverse cross section.

8. A double lumen catheter comprising an elongated unitary cylindrical tube having a longitudinal planar axial septum of one-piece construction with said tube, said septum dividing the interior of said tube into first and second lumens, the proximal end of said cylindrical tube connecting to two separate tubes communicating with the respective first and second lumens for the injection and removal of fluid, the first lumen extending from the proximal end of said cylindrical tube to an opening at the distal end of said cylindrical tube and the second lumen extending from the proximal end of said cylindrical tube to a second opening spaced a sufficient distance away from said first opening, in the longitudinal direction, to prevent mixing of the returned blood with the blood taken in, the distal end of said tube having a blunt end to prevent the end of the catheter from traumatizing or becoming caught in the walls of a blood vessel into which the catheter is inserted, and wherein the second lumen has a solid terminal portion distal to said second opening and formed so that no voids are present in the blood flow path, and said cylindrical tube has a uniform diameter from said proximal end to said distal end.

9. The double lumen catheter as claimed in claim 8, wherein the first and second lumens are semicircular in cross section.

10. A double lumen catheter as claimed in claim 8, wherein the opening at the distal end of said cylindrical tube is eccentric with respect to the axis of the cylindrical tube.

11. A double lumen catheter comprising an elongated unitary cylindrical tube including a planar axial divider bisecting said cylindrical tube into first and second lumens, the proximal end of said cylindrical tube connecting two separate tubes communicating with the respective first and second lumens for the injection and removal of fluid, the first lumen extending from the proximal end of said cylindrical tube to a first opening at the distal end of said cylindrical tube, the second lumen extending from the proximal end of said cylindrical tube to a second opening spaced a sufficient distance away from said first opening, in the longitudinal direction, to prevent mixing of the returned blood with the blood taken in, the distal end of said tube having a blunt end to prevent the end of the catheter from traumatizing or becoming caught in the walls of a blood vessel into which the catheter is inserted, and wherein the second lumen has a solid terminal portion distal to said second opening and formed so that no voids are present in the blood flow path, and said cylindrical tube has a uniform diameter from said proximal end to said distal end.

12. The double lumen catheter as claimed in claim 11, wherein the first opening in the distal end of said cylindrical tube is eccentric with respect to the axis of the cylindrical tube.

13. The double lumen catheter as claimed in claim 11, wherein the first and second lumens are semicircular in cross section.

* * * * *

UNITED STATES PATENT AND TRADEMARK OFFICE
CERTIFICATE OF CORRECTION

PATENT NO. : 5,197,951

DATED : Mar. 30, 1993

INVENTOR(S) : Sakharam D. Mahurkar

It is certified that error appears in the above-identified patent and that said Letters Patent is hereby corrected as shown below:

The title page, showing the illustrative figure, should be deleted and substitute therefor the attached title page.

Signed and Sealed this

Fifth Day of October, 1993

Attest:

BRUCE LEHMAN

Attesting Officer

Commissioner of Patents and Trademarks

United States Patent [19]

Mahurkar

[11] Patent Number: 5,197,951
[45] Date of Patent: Mar. 30, 1993

[54] SIMPLE DOUBLE LUMEN CATHETER

[76] Inventor: Sakharam D. Mahurkar, 6171 N. Sheridan Rd. - #1112, Chicago, Ill. 60660

[21] Appl. No.: 834,202

[22] Filed: Feb. 27, 1986

Related U.S. Application Data

[63] Continuation of Ser. No. 561,480, Dec. 14, 1983, abandoned.

[51] Int. Cl.$^5$ .............................................. A61M 11/00
[52] U.S. Cl. ...................................... 604/93; 604/43; 604/283; 606/94
[58] Field of Search ............................ 604/93, 43–45, 604/280–282; 606/191, 192

[56] References Cited

U.S. PATENT DOCUMENTS

| D. 250,349 | 11/1978 | McFarlane | D24/54 |
| D. 254,444 | 3/1980 | Levine | D24/54 |
| 256,590 | 4/1882 | Pfarre | |
| D. 256,617 | 8/1980 | Clemens | D24/54 |
| D. 272,651 | 2/1984 | Mahurkar | |

(List continued on next page.)

FOREIGN PATENT DOCUMENTS

| 834211 | 2/1976 | Belgium | 128/221 |
| 1092927 | 1/1981 | Canada | 604/43 |
| 50089 | 8/1982 | Canada | |
| 1150122 | 7/1983 | Canada | 128/81 |
| 1167727 | 5/1984 | Canada | 128/80 |
| 36642 | 9/1981 | European Pat. Off. | 604/43 |
| 0079719 | 11/1982 | European Pat. Off. | |
| 935625 | 11/1955 | Fed. Rep. of Germany | |
| 2259865 | 6/1974 | Fed. Rep. of Germany | 128/221 |
| MR19346 | 6/1982 | Fed. Rep. of Germany | |
| 592193 | 4/1925 | France | 128/214.2 |
| 1285953 | 7/1962 | France | |
| 1508959 | 1/1968 | France | |
| 2285148 | 4/1976 | France | |
| 2297640 | 8/1976 | France | |
| 821344 | 4/1982 | France | |
| 55-88771 | 7/1980 | Japan | 128/348 |
| 688450 | 3/1952 | United Kingdom | |
| 1419702 | 12/1975 | United Kingdom | 128/221 |
| 1006219 | 3/1983 | United Kingdom | |
| 1017315 | 5/1983 | U.S.S.R. | |

OTHER PUBLICATIONS

McIntosh et al., "Double Lumen Catheter," *J.A.M.A.*, Feb. 21, 1959, pp. 137/835–138/836.

*Dorland's Illustrated Medical Dictionary*, 25th Ed., W. B. Saunders Co., Philadelphia, 1974, p. 274.
Brenner & Rector, *The Kindney*, vol. III, W. B. Saunders Co., Philadelphia, 1976, p. 164.
*ASAIO Abstracts*, vol. 5, 22nd Annual Meeting, San Franciso, Calif., Apr. 1–3, 1976, p. 52.
Tohuko, J., "Single Two-Lumen Cannula Dialysis", Aug. 1974.
Tsuchida et al., "Single Two-Lumen Cannula Dialysis", Toboku Journal Exp Med., 1974, pp. 114, 159–101.
Tsuchida et al. "Design of a Two-Lumen-Piercing Needle That Is Capable of Carrying Out Dialysis By Single Puncture", Journal of The Urological Society of Japan, vol. 65 (12), 1974, pp. 805–807.
Kaplan et al., "A Co-Axial Dual Flow Catheter/Cannula For Single Puncture Dialysis", Dialysis & Transplantation, Dec./Jan. 1977, pp. 38–40, 42, 84.
"Terumo Coaxial Dual Flow Catheter", Terumo America, Inc., Apr., 1979 (two pages).
"Portner-Koolpe Biliary Biopsy Set", Cook Inc. (1 page).

*Primary Examiner*—C. Fred Rosenbaum
*Assistant Examiner*—Chalin Smith
*Attorney, Agent, or Firm*—Arnold, White & Durkee

[57] ABSTRACT

A double lumen catheter comprising an elongated cylindrical tube enclosing first and second lumens separated by an internal divider, the proximal end of the elongated tube connecting to two separate connecting tubes communicating with the respective first and second lumens for the injection and removal of blood, the first lumen extending from the proximal end of the elongated tube to a first opening formed in the side wall of the tube and at the distal end of the elongated tube, and the second lumen extending from the proximal end of the elongated tube to a second opening spaced a sufficient distance away from the first opening, in the longitudinal direction, to prevent mixing of the returned blood with the blood taken in, the distal end portion of the tube beyond the distal end of the second lumen continuing the cylindrical configuration of the tube to the distal end of the first lumen so as to form a blunt circular end on the tube to prevent the end of the catheter from traumatizing or becoming caught in the walls of a blood vessel into which the catheter is inserted.

13 Claims, 1 Drawing Sheet